United States Patent [19]

Schilling et al.

[11] 4,093,642

[45] June 6, 1978

[54] SURFACE ACTIVE SILICONES

[75] Inventors: Curtis L. Schilling, Croton-on-Hudson; Bela Prokai, Mahopac; Bernard Kanner, West Nyack, all of N.Y.

[73] Assignee: Union Carbide Corporation, New York, N.Y.

[21] Appl. No.: 752,879

[22] Filed: Dec. 20, 1976

[51] Int. Cl.$^2$ .............................................. C07F 7/10
[52] U.S. Cl. .............................. 544/106; 260/448.2 N
[58] Field of Search ................. 260/448.2 N, 247.1 R, 260/247.1 E

[56] References Cited

U.S. PATENT DOCUMENTS

| | | | |
|---|---|---|---|
| 3,278,465 | 10/1966 | Twitchett et al. | 260/448.2 N X |
| 3,389,160 | 6/1968 | Reid | 260/448.2 N |
| 4,006,176 | 2/1977 | Heckert et al. | 260/448.2 N |

*Primary Examiner*—Paul F. Shaver
*Attorney, Agent, or Firm*—Dale Lynn Carlson

[57] ABSTRACT

This invention relates to ion-pair-containing siloxane compounds that are extremely effective as surface tension depressants. The compounds of the present invention contain both anionic and cationic substituents and can be formed by metathesis reactions between metallic salts of anionic silicone or organic surface-active compounds and halide salts of quaternary ammonium silicone or organic surface-active compounds. The compounds of the invention are relatively pH insensitive when compared to siloxanes bearing anionic and cationic substituents that are formed by proton transfer. Thus, the organosilicon compounds of the invention will remain stable despite changes in pH of the mixture in which they are present.

10 Claims, No Drawings

SURFACE ACTIVE SILICONES

DESCRIPTION OF THE PRIOR ART

Heretofore a wide variety of siloxane compounds containing anions and cations have been made. However, such compounds have been formed by proton (hydrogen ion) transfer from an acid group to an amine group or one of the ions has not been surface active. As a result, the compounds have not been stable to pH changes or have had ions that essentially dilute the surface activity of the compound.

For example, U.S. Pat. No. 3,389,160 discloses dialkylamino hydroxy organosilicon salts of carboxylic acids of one to six carbon atoms, and it also discloses quaternary ammonium halide derivatives of dialkylamino hydroxy organsilicon compounds. The dialkylamino hydroxy organosilicon salts of carboxylic acids disclosed in that patent are formed by proton transfer. The quaternary ammonium halide derivatives of dialkylamino hydroxy organosilicon compounds of that patent have halide anions that are not surface active.

As further examples, U.S. Pat. No. 3,303,048 discloses aminoalkylsiloxane salts of carboxylic acids such as decoic, oleic, and stearic acids. The siloxane salts of that patent are also formed by proton transfer from an acid group to an amine group.

As a still further example, British Pat. No. 1,056,066 discloses oxypropylated triethanolamine salts of siloxane carboxylic acids derived from the hydrolysis of addition products of maleic anhydride and hydroxysiloxanes. Again, this patent discloses siloxane salts formed by proton transfer from an acid group to an amine group.

As an additional example, U.S. Pat. No. 3,278,465 discloses a broad class of siloxanes containing ion pairs as surfactants in the manufacture of cellular polyurethanes. However, none of the silicon-free counterions in the specifically disclosed siloxanes are surface active. Further, no disclosure is made of the advantage inherent in polysiloxanes containing ion pairs wherein both ion and counterion are surface active.

SUMMARY OF THE INVENTION

This invention relates to novel organosilicon compounds containing surface-active anionic and cationic substituents. These compounds are formed by metathesis reactions between metallic salts of anionic silicone or organic surface-active compounds and halide salts of quaternary ammonium silicone or organic surface-active compounds. The novel compounds fall into two classes.

One class of compounds of this invention is represented by the following formula:

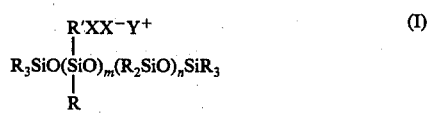
(I)

where
(1) R is a monovalent hydrocarbon group having from 1 to 18 carbon atoms,
(2) R' is a divalent organic group whose valences are provided by carbon atoms and having from 1 to 18 carbon atoms,
(3) $XX^-$ is a divalent anionic group covalently bonded to R' and ionically bonded to $Y^+$,
(4) $Y^+$ is a monovalent cation that has at least 8 carbon atoms and that is derived from a cationic surfactant having a halogen counterion by removal of the halogen, and that is free of ionically-bonded hydrogen,
(5) $m$ is an integer having a value from 1 to 100 (preferably from 1 to 5),
(6) $n$ is an integer having a value from 0 to 200 (preferably from 0 to 10), and
(7) the ratio of $m$ to $(n+2)$ being at least 0.1 to 20 (preferably at least 0.1 to 0.5).

The other class of compounds of this invention is represented by the following formula:

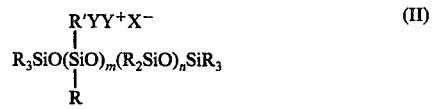
(II)

where
(1) R is a monovalent hydrocarbon group having from 1 to 18 carbon atoms,
(2) R' is a divalent organic group whose valences are provided by carbon atoms and having from 1 to 18 carbon atoms,
(3) $YY^+$ is a divalent cationic group that is free of ionically-bonded hydrogen and that is covalently bonded to R' and ionically bonded to $X^-$,
(4) $X^-$ is a monovalent anion that has at least 8 carbon atoms and that is derived from an anionic surfactant having a monovalent metal counterion by removal of the metal,
(5) $m$ is an integer having an average value from 1 to 100 (preferably from 1 to 5),
(6) $n$ is an integer having a value from 0 to 200 (preferably from 0 to 10), and
(7) the ratio of $m$ to $(n+2)$ being at least 0.1 to 20 (preferably at least 0.1 to 0.5).

DESCRIPTION OF THE PREFERRED EMBODIMENTS

Suitable monovalent hydrocarbon groups represented by R in Formulas I and II above include alkyl, alkenyl, aryl, alkaryl, or aralkyl groups. Illustrative monovalent hydrocarbon groups from which R can be selected are: methyl, ethyl, propyl, isobutyl, decyl, octadecyl, cyclopentyl, cyclohexyl, naphthyl, vinyl, butenyl, cyclohexenyl, tolyl, xylyl, benzyl and beta-phenylethyl. Preferably R is methyl.

Suitable divalent organic radicals represented by R' in Formulas I and II above are the alkylene, arylene or aralkylene radicals; suitable divalent hydrocarbonoxy radicals represented by R' are the same as the hydrocarbon radicals except that they also contain one or more ether lnkages linkages —CH₂—O—CH₂—) and/or hydroxyl substituents. Thus, R' can be an alkylene group such as methylene, ethylene, propylene, 2- methylpropylene or butylene; it can be an arylene group such as phenylene; it can be an aralkylene group such as phenyl methylene or it can be a divalent hydrocarbonoxy radical having the formula —(CH₂)₃OCH₂CHOHCH₂— or
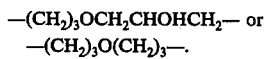

In regard to the portion of Formulas I and II depicted as $(R_2SiO)_n$, the monovalent hydrocarbon groups represented by R may be the same or different on each siloxane moiety. In addition, these hydrocarbon groups may be the same or different with respect to different siloxane moieties within the same compound.

In Formula I suitable monovalent cations represented by Y+ include Me$_3$N+R (e.g. Me$_3$N+C$_{12}$H$_{25}$) and R$_4$N+ (e.g. (C$_{12}$H$_{25}$)$_4$N+) wherein R is defined above, with the proviso that at least one R group in each cation have at least 8 carbon atoms. In addition, suitable monovalent cations include the class of cations represented by the formula:

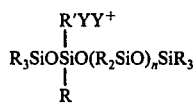

wherein R, R', YY+ and n are defined in Formula II above.

In Formula II suitable monovalent anions represented by X− include −O$_2$CR (e.g., —O$_2$C$_8$H$_{17}$) and −O$_4$SR (e.g., −O$_4$SC$_8$H$_{17}$, −O$_4$SC$_{10}$H$_{21}$, −O$_4$SC$_{12}$H$_{25}$) wherein R is defined above, with the proviso that at least one R group in each anion have at least 8 carbon atoms. In addition, suitable monovalent anions include the class of anions represented by the formula:

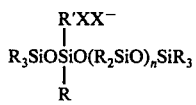

wherein R, R', XX− and n are defined in Formula II above.

In Formula II above suitable divalent cationic groups represented by YY+ include +NR$_3$ (such as +NMe$_3$) wherein R is defined above;

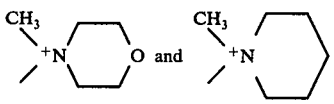

As is shown by the above formulas, the compounds of this invention are ion-pair containing compounds in which each of the substituents is a surfactant and can be either silicone or organic.

As is mentioned above, the novel organosilicon compounds of the invention are formed by metathesis reactions between metallic salts of anionic silicone or organic surface-active compounds and halide salts of quaternary ammonium silicone or organic surface-active compounds. Thus, the compounds of the instant invention are not formed by proton transfer and neither ion in the ion pair contains acidic protons. The process of forming the compounds of the invention as given in Formulas I and II above is illustrated below using specific reactants:

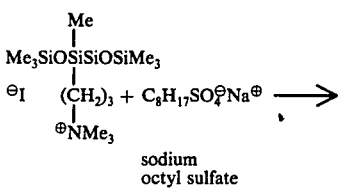

sodium octyl sulfate

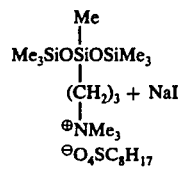

cationic silicone-anionic organic species

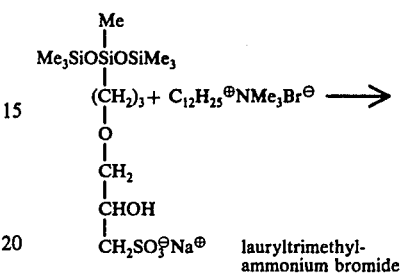

lauryltrimethylammonium bromide

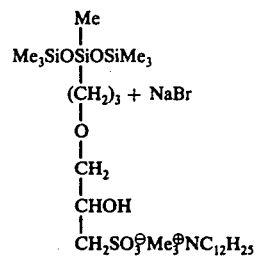

anionic silicone-cationic organic species

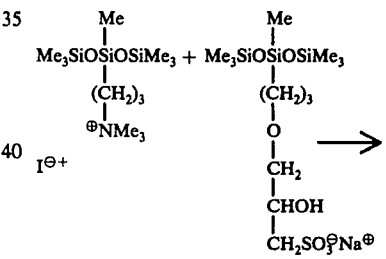

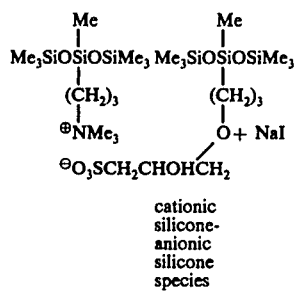

cationic silicone-anionic silicone species

The process of the invention is performed by combining equimolar amounts of the respective ionic reactants in the presence of solvents. The solvents used may be water miscible, such as low molecular weight alcohols and acetone, or water may be used as the sole solvent. When water alone is used, the product may precipitate and be isolated by filtration. Otherwise, the more volatile solvents are stripped and the residue is extracted with an organic solvent immiscible with water such as ethyl ether, chloroform, carbon tetrachloride, benzene or toluene. Water may be added to aid in phase separation and removal of inorganic salts. The extraction solutions are then filtered and solvent stripped, leaving products in the form of waxy solids or very viscous semi-solids.

Although a wide range of temperatures may be used in the process of the invention, ranging from 0° to 200° C, there is no advantage to the use of high or low temperatures. Therefore, room temperature is the preferred temperature for the process of the invention. Atmospheric pressure is used unless low boiling solvents are used.

The process of this invention is applicable to any silicone or organic, anionic or cationic, surfaceactive reactants. Although Formulas I and II are restricted to monoanionic and monocationic ion-pair compounds when $x=1$, the invention is also applicable to polyanionic and polycationic compounds (see Example VII below) when $x$ is greater than 1, with the proviso that if one reactant is polyanionic or polycationic, the other reactant (of opposite charge) must be monocationic or monoanionic, respectively.

Typical examples of anionic and cationic silicone reactants are given in U.S. Pat. Nos. 3,389,160 patented June 18, 1968; 3,507,897 patented Apr. 20, 1970; 3,658,867 patented Apr. 25, 1972; and 3,660,452 patented May 2, 1972, all incorporated herein by reference.

The compounds of the instant invention are useful in solution using aqueous and non-aqueous solvents. Therefore, it is not necessary to isolate the compositions of the invention. Instead, the compounds of the invention can be used in the solutions in which they are prepared. Since the compounds of the invention are useful in the presence of the surface-inactive metallic halide by-products of the invention, it is not necessary to remove these halides from solution.

The organosilicon compounds of the present invention are useful as aqueous surface tension depressants, having limiting surface tensions in water of 20.8 to 22.5 dyne/cm. with very low critical micelle concentrations of 0.0005 to 0.05 weight percent. At these low concentrations they are much more effective aqueous surface tension depressants than conventional ionic silicone or organic surfactants.

The compounds of the invention are potentially useful in a wide variety of other surface related areas such as water-washable lubricants, mold release agents, wetting agents, bactericides, detergent additives, foam stabilizers, anti-static agents, and as additives to coatings, paints and polishes. In addition, the compounds of the invention have shown effectiveness as emulsifiers for water-hydrocarbon, water-halocarbon, and water-silicone oil mixtures.

As used herein, "surfactant" denotes a material that lowers the bulk surface tension of water to below 40 dynes per centimeter at a concentration of 0.1 parts by weight or lower of the material per 100 parts of water at 25° C. Such a definition of surfactants appears in A. M. Schwartz and J. W. Perry, *Surface Active Agents*, Vol. 1, p. 282 (1949).

As used herein, "Me" denotes the methyl group, "g" denotes grams, and % denotes weight percent.

The following examples are given by way of illustration only in order to describe the invention in greater detail, and are not intended to limit the scope thereof.

EXAMPLE I 18.7 g. (0.042 mole) of $(Me_3SiO)_2MeSi(CH_2)_3{}^+NMe_3I^-$ were dissolved in 200 ml. of acetone and combined with a mixture containing 9.7 g. (0.042 mole) of sodium octyl sulfate $(C_8H_{17}SO_4Na)$ in 125 ml. of water. The acetone was removed under aspirator vacuum, and a two phase mixture remained. Following extraction of the mixture with carbon tetrachloride $(CCl_4)$, filtration, stripping, and vacuum drying, 21.2 g. of product was obtained (95.5%) yield. The product was a waxy yellow solid which upon analysis was determined to be $(Me_3SiO)_2MeSi(CH_2)_3{}^+NMe_3{}^-O_4SC_8H_{17}$.

The product had a limiting aqueous surface tension of 22.2 dyne/cm.

EXAMPLE II

A mixture of 150g. of 40% active $(Me_3SiO)_2MeSi(CH_2)_3OCH_2CHOHCH_2SO_3{}^-Na^+$ (in 9:5 ethanol:water), 40 g. of lauryltrimethylammonium bromide, and 50 ml. of water was extracted with benzene. The benzene was evaporated, and the residue was extracted with $CCl_4$ and the extract was treated with "Hyflo Supercel" (a filtration aid) and the resulting mixture was filtered and vacuum stripped. The product was an opaque white paste, having the formula: $(Me_3SiO)_2MeSi(CH_2)_3OCH_2CHOHCH_2SO_3{}^-Me_3{}^+NC_{12}H_{25}$.

The product had a limiting aqueous surface tension of 20.7 dyne/cm. and a critical micelle concentration of 0.02 wt. percent.

A mixture of 10 ml. of water, 10 ml. of benzene, and 0.2 g. of product formed an emulsion when shaken which was stable for several days. The product also acted as an emulsifying agent for water-silicone oil and water-$CCl_4$.

EXAMPLE III

A mixture of 60 g. of 40% active $(Me_3SiO)_2MeSi(CH_2)_3OCH_2CHOHCH_2SO_3{}^-Na^+$ (in 9:5 ethanol:water) and 40 g. of 60% active $(Me_3SiO)_2MeSi(CH_2)_3OCH_2CHOHCH_2{}^+NMe_3Cl^-$ (in ethanol) and 3 l. of water was made. The precipitated oily product was extracted with $CCl_4$. The extract was treated with "Hyflo Supercel", filtered, and vacuum stripped to yield 24.3 g. of a clear, very viscous semisolid product (55% yield).

The product had a limiting aqueous surface tension of 20.8 dyne/cm, and a critical micelle concentration 0.04 wt. %.

EXAMPLE IV

A mixture of 143 g. of 60% active $(Me_3SiO)_2MeSi(CH_2)_3OCH_2CHOHCH_2{}^+NMe_3Cl^-$ (in ethanol) and 200 g. of 50% active $(Me_3SiO)_2MeSi(CH_2)_3OCH_2CHOHCH_2N(CH_3)CH_2CH_2SO_3{}^-Na^+$ (in 2.4:1 isopropanol: water) was stripped under vacuum in order to remove the ethanol and isopropanol. The remainder was extracted twice with 500 ml. portions of $CCl_4$. The extract was treated with "Hyflo Supercel", filtered, vacuum stripped, and vacuum dried overnight at 65° C. The product was a clear tan solid having the formula $(Me_3SiO)_2MeSi(CH_2)_3OCH_2CHOHCH_2{}^+NMe_3{}^-{}^\lambda O_3SCH_2CH_2N(CH_3)CH_2CHOHCH_2O(CH_2)_3SiMe(OSiMe_3)_2$.

The product had a limiting aqueous surface tension of 21.2 dyne/cm., and it was an effective emulsifying agent at 0.5 wt. % for equal volumes of benzene and water.

EXAMPLE V 143 g. of 60% active $(Me_3SiO)_2MeSi(CH_2)_3OCH_2CHOHCH_2{}^+NMe_3Cl^-$ (in ethanol), and 53 g. of sodium decyl sulfate $(C_{10}H_{21}SO_4Na)$ were combined with 100 ml. of H₂O. The mixture was vacuum stripped and the resultant gelatinous mass was taken up in CCl₄. Phase separation occurred. The CCl₄ phase was washed with 150 ml of H₂O, followed by treatment with "Hyflo Supercel", filtration, stripping, and vacuum drying overnight.

The product was a clear tan paste having the formula:
(Me₃SiO)₂MeSi(CH₂)₃OCH₂CHOHCH₂⁺NMe₃-⁻O₄SC₁₀H₂₁.

The product had a limiting aqueous surface tension of 21.8 dyne/cm.

EXAMPLE VI

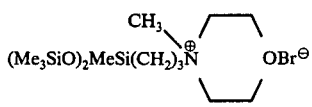

(22.2 g., 0.05 mole) and sodium dodecyl sulfate (14.4 g., 0.05 mole), C₁₂H₂₅SO₄Na) as separate solutions, each in 80 ml. of water, were combined. The product precipitated as a waxy solid, which was taken up in methanol. Filtration, stripping, and vacuum drying, yielded the product,

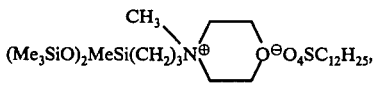

a waxy, white solid (27.2 g., 86.4% yield).

EXAMPLE VII

A polycationic silicone fluid, Me₃SiO (Me₂SiO)₁₈₀-(MeYSiO)₂₀SiMe₃, were Y is —(CH₂)₃OCH₂CH₂⊕-NMe₃⊖I, (13.1 g.) was dissolved in 40 ml. dry ethanol. The ethanol solution was combined with a solution of 3.8 g. sodium dodecyl sulfate (C₁₂H₂₅SO₄Na) in 20 ml. 50% aqueous ethanol. The combined solution was stirred, and 175 ml. H₂O added, causing the precipitation of an oily solid. CCl₄ extraction, filtration (after addition of a trace of ethanol for clarity), vacuum stripping, and vacuum drying overnight at 60° yielded 13.5 g. (88%) of product, having the formula: Me₃SiO(Me₂SiO)₁₈₀(MeY'SiO)₂₀SiMe₃ where Y' is —(CH₂)₃OCH₂CH₂⊕NMe₃⊖O₄SC₁₂H₂₅.

This polyfunctional ion-pair product was insoluble in pure water, reflecting its higher molecular weight. It was effective as an emulsifier for water-halocarbon and water-silicone oil mixtures.

What is claimed is:

1. A composition of matter selected from the group consisting of:

A. Siloxane compounds having the structural formula:

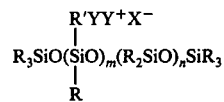

where
(1) R is a monovalent hydrocarbon group having from 1 to 18 carbon atoms,
(2) R' is a divalent organic group whose valences are provided by carbon atoms and having from 1 to 18 carbon atoms,
(3) XX⁻ is a divalent anionic group covalently bonded to R' and ionically bonded to Y⁺,
(4) Y⁺ is a monovalent cation that has at least 8 carbon atoms and that is derived from a cationic surfactant having a halogen counterion by removal of the halogen and that is free of ionically-bonded hydrogen,
(5) m is an integer having a value from 1 to 100,
(6) n is an integer having a value from 0 to 200,
(7) the ratio of m to (n+2) being from 0.1 to 20, and B. Siloxane compounds having the structural formula:

$$\begin{array}{c} R'YY^+X^- \\ | \\ R_3SiO(SiO)_m(R_2SiO)_nSiR_3 \\ | \\ R \end{array}$$

where
(1) R is a monovalent hydrocarbon group having from 1 to 18 carbon atoms,
(2) R' is a divalent organic group whose valences are provided by carbon atoms and having from 1 to 18 carbon atoms,
(3) YY⁺ is a divalent cationic group that is free of ionically-bonded hydrogen and that is covalently bonded to R' and ionically bonded to X⁻,
(4) X⁻ is a monovalent anion that has at least 8 carbon atoms and that is derived from an anionic surfactant having a monovalent metal counterion by removal of the metal,
(5) m is an integer having an average value from 1 to 100,
(6) n is an integer having a value from 0 to 200, and
(7) the ratio of m to (n+2) being from 0.1 to 20.

2. A composition of matter as defined in Part A of claim 1.

3. A composition of matter as defined in Part B of claim 1.

4. A composition of matter as claimed in Part A of claim 1 wherein R is methyl, R' has the formula —(CH₂)₃OCH₂CHOHCH₂—, m has a value from 1 to 50 and n has a value of 0.

5. A composition of matter as claimed in Part B of claim 1 wherein R is methyl, R' has the formula —(CH₂)₃OCH₂CHOHCH₂—, m has a value from 1 to 50 and n has a value of 0.

6. A composition of matter as defined in claim 2 having the structural formula: (Me₃SiO)₂ MeSi(CH₂)₃OCH₂CHOHCH₂SO₃⁻Me₃⁺NC₁₂H₂₅

7. A composition of matter as defined in claim 2 having the structural formula: (Me₃SiO)₂MeSi(CH₂)₃OCH₂CHOHCH₂SO₃⁻Me₃⁺NCH₂CHOHCH₂O—(CH₂)₃ MeSi(Me₃SiO)₂

8. A composition of matter as defined in claim 3 having the structural formula: (Me₃SiO)₂MeSi (CH₂)₃OCH₂CHOHCH₂⁺NMe₃⁻O₃SCH₂CH₂N—(CH₃)CH₂-CHOHCH₂O(CH₂)₃SiMe(OSiMe₃)₂

9. A composition of matter as defined in claim 3 having the structural formula: (Me₃SiO)₂MeSi(CH₂)₃OCH₂CHOHCH₂⁺NMe₃⁻O₄SC₁₀H₂₁

10. A composition of matter as defined in claim 3 having the structural formula:

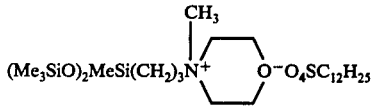

* * * * *